United States Patent [19]

Beeley et al.

[11] 4,442,126
[45] Apr. 10, 1984

[54] 1,2,3,4-TETRAHYDRONAPHTHALENE DERIVATIVES

[75] Inventors: Nigel R. A. Beeley, Villebon sur Yvette; Gérard Cremer, Chilly Mazarin; Michael J. Dimsdale, Villebon sur Yvette; Philippe Manoury, Le Plessis Robinson, all of France

[73] Assignee: Synthelabo, Paris, France

[21] Appl. No.: 418,265

[22] Filed: Sep. 15, 1982

[30] Foreign Application Priority Data

Sep. 16, 1981 [FR] France ............... 81 17454

[51] Int. Cl.³ ............... A61K 31/165; C07C 103/365
[52] U.S. Cl. ............... 424/324; 564/222; 564/428; 424/330
[58] Field of Search ............... 564/222, 428; 424/324, 424/330

[56] References Cited

U.S. PATENT DOCUMENTS 3,991,207 11/1976 Sarges et al. ............... 564/428
4,320,148 3/1982 De Marinis ............... 564/222

FOREIGN PATENT DOCUMENTS 2803582 8/1979 Fed. Rep. of Germany ...... 424/330
53-46947 4/1978 Japan ............... 564/428
54-5959 1/1979 Japan ............... 424/330

OTHER PUBLICATIONS

*Chemical Abstracts*, vol. 54, Abstract No. 7659d, 1955, Ward, E. R. et al., "Isomer Ratios in the Nitration of 6-Acylamino-1,2,3,4-tetrahydronaphthalene".
*Chemical Abstracts*, vol. 65, Abstract No. 663c, 1966, Hecker et al., "Radical Hydroxylation of 6-Tetralol with Fenton's Reagent".

*Primary Examiner*—Natalie Trousof
*Assistant Examiner*—Patricia M. Scott
*Attorney, Agent, or Firm*—Wegner & Bretschneider

[57] ABSTRACT

New compounds of the formula:

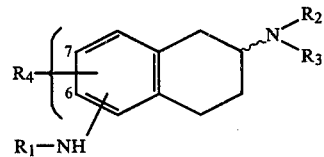

wherein $R_1$ represents a hydrogen atom or an alkanoyl group containing from 1 to 4 carbon atoms, $R_2$ and $R_3$ each represent a hydrogen atom or a $C_1$–$C_4$ alkyl group, and $R_4$ represents a hydroxy or methoxy group in the 6-position or 7-position, have been found to be useful in therapy, and more particularly in the treatment of cardiovascular diseases and Parkinson's disease.

8 Claims, No Drawings

1,2,3,4-TETRAHYDRONAPHTHALENE DERIVATIVES

DESCRIPTION

The present invention relates to new therapeutically useful 2-amino-1,2,3,4-tetrahydronaphthalene derivatives, to processes for their preparation and pharmaceutical compositions containing them.

The 2-amino-1,2,3,4-tetrahydronaphthalene derivatives of the present invention are those compounds of the general formula:

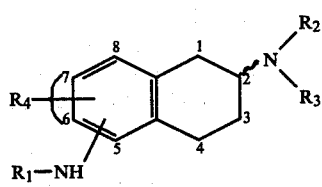

wherein $R_1$ represents a hydrogen atom or an alkanoyl group containing from 1 to 4 carbon atoms, $R_2$ and $R_3$ each represent, independently of one another, a hydrogen atom or an alkyl group containing from 1 to 4 carbon atoms, and $R_4$ represents a hydroxy or methoxy group located in the 6-position or 7-position, and their pharmacologically-acceptable acid addition salts.

As the compounds of the invention of general formula (I) contain an asymmetric carbon atom in their molecule (2-position), they can be in the form of racemates or enantiomers.

The preferred compounds of the invention are those of general formula (I) wherein $R_1$ represents the formyl (i.e. —CHO) or acetyl (i.e. —COCH$_3$) group, and $R_2$ and $R_3$ each represent a propyl group, and more especially those compounds in which the group $R_4$ is the 6-position and the group —NHR$_1$ is in the 5-position. Preferably $R_4$ is the hydroxy group. An outstanding compound of the invention is 2-dipropylamino-5-formylamino-6-hydroxy-1,2,3,4-tetrahydronaphthalene.

Those compounds of general formula (I) wherein $R_2$ and $R_3$ both represent hydrogen atoms or alkyl groups (viz. the grouping —NR$_2$R$_3$ represents a primary amino or dialkylamino group) can be prepared by reacting 6-methoxy- or 7-methoxy-1,2,3,4-tetrahydronaphthalen-2-one, which are commercially available products, corresponding to the formula:

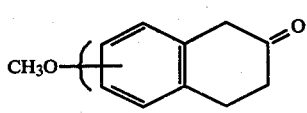

(wherein the methoxy group is located in the 6- or 7-position) with benzylamine or a dialkylamine of the general formula:

(wherein $R'_2$ and $R'_3$ each represent an alkyl group containing from 1 to 4 carbon atoms) to give a 2-amino-6(or 7)-methoxy-3,4-dihydronaphthalene of the general formula:

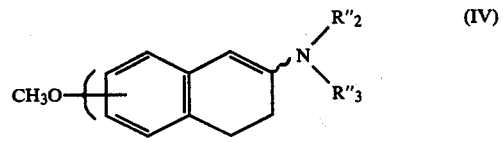

(wherein $R''_2$ and $R''_3$ both represent hydrogen atoms or both represent alkyl groups containing from 1 to 4 carbon atoms) and hydrogenating such a compound under pressure to give a 2-amino-tetrahydronaphthalene of the general formula:

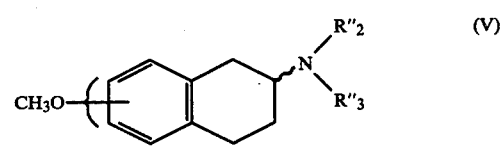

wherein $R''_2$ and $R''_3$ are as hereinbefore defined, and the methoxy group is located in the 6- or 7-position.

The compounds of general formula (V) wherein $R''_2$ and $R''_3$ represent identical alkyl groups can also be obtained by alkylation of a corresponding 2-amino compound of general formula (V) wherein $R''_2$ and $R''_3$ both represent hydrogen atoms. The alkylation can be carried out in a manner known per se, for example by reacting a suspension of an acid addition salt of the primary amine (V) with an appropriate alkyl halide containing 1 to 4 carbon atoms, preferably the iodide, in the presence of a base such as potassium carbonate. This method of preparation is to be preferred when it is desired to prepare a single enantiomer of a compound of general formula (I) wherein $R_2$ and $R_3$ both represent the same alkyl group. In fact, it is easier to separate the enantiomers of the primary amine of general formula (V) (i.e. the grouping —NR''$_2$R''$_3$ is —NH$_2$) than the enantiomers of the final compound.

The amino compound of general formula (V) is then subjected to nitration. This produces a mixture of two isomers nitrated respectively in the 5-position and 7-position if the methoxy group is in the 6-position, or in the 6-position and 8-position if the hydroxy group is in the 7-position, according to the general formula:

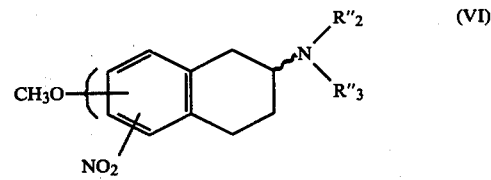

wherein $R''_2$ and $R''_3$ are as hereinbefore defined, and the methoxy group is located in the 6- or 7-position.

The nitro derivatives of the general formula (VI) are new compounds and also form part of the present invention.

If desired, one of the nitro derivatives is then demethylated after it has been separated from its isomer, and this gives an acid addition salt of the 6(or 7)-hydroxy-2-aminotetrahydronaphthalene of the general formula:

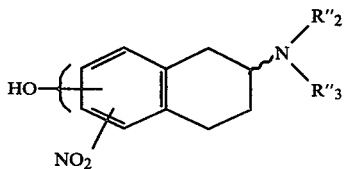

wherein R″₂ and R″₃ are as hereinbefore defined.

Catalytic reduction (Pd, Raney Ni) of the nitro group of the compound of general formula (VI) or (VII) results in the diamine of the general formula:

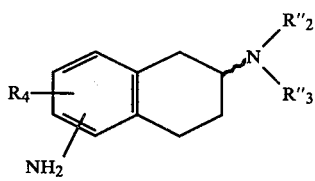

(wherein R″₂, R″₃ and R₄ are as hereinbefore defined) which is finally subjected, if desired, to N-acylation by means of an acid of the general formula R′₁—OH (wherein R′₁ represents an alkanoyl group containing from 1 to 4 carbon atoms), or an acylating derivative thereof, to give a compound of general formula (I).

The condensation of benzylamine or the dialkylamine of general formula (III) with the tetrahydronaphthalene of formula (II) can be carried out under the action of heat in a non-polar solvent, such as benzene, in the presence of an acid such as para-toluenesulphonic acid. Hydrogenation of the resulting compound is then carried out in the same reaction vessel in the presence of a hydrogenation catalyst and under pressure.

The nitration of the 2-aminotetrahydronaphthalene of general formula (V) can be carried out in a manner known per se. If the amino group is not alkylated (R″₂ and R″₃=H), the amino group should be protected beforehand by acylating it, for example by means of acetic anhydride, and then by removing the acetyl group at the end of the nitration. The two nitro isomers of general formula (VI) are then separated in a known manner, for example by column chromatography.

Demethylation of a nitro compound of formula (VI), separated from its isomer, can be carried out, for example, by reaction with hydrobromic acid or by reaction with boron tribromide, followed by salification.

The nitro group of the compound of general formula (VII) is then reduced with hydrogen in the presence of a catalyst such as palladium on a carbon support, and also under pressure.

Finally, acylation of a compound of general formula (VIII) producing a final compound of general formula (I) wherein R₁ represents an alkanoyl group can be carried out in a known manner, in the cold, with formic or acetic acid, in the presence of acetic anhydride, or with the anhydride of a higher acid.

The compounds of the invention of general formula (I) wherein —NR₂R₃ denotes a monoalkylamino group can be prepared from a primary amine of general formula (V) (—NR″₂R″₃=NH₂), in the form of a racemate or an enantiomer.

Before carrying out the nitration of the benzene ring, the —NH₂ group of the compound of general formula (V) is acylated, not with any acid as in the case where the final compound of general formula (I) is to have a primary amino group in the 2-position, but by choosing the C₁₋₄ aliphatic acid, or one of its acylating derivatives, in which the number of carbon atoms corresponds to the length only of the alkyl group R₂ (or R₃) of the compound of general formula (I) to be prepared. After the nitration, the separation of the nitro isomers and the reduction of one of them to the primary amine by catalytic hydrogenation, the alkanoylamino group in the 2-position is reduced to the monoalkylamino group —NR₂R₃ (wherein one of the symbols R₂ and R₃ represents hydrogen and the other represents an alkyl group containing from 1 to 4 carbon atoms), for example with lithium aluminium hydride.

Finally, before carrying out the final acylation of the —NH₂ group on the benzene ring with an acid R′₁—OH (wherein R′₁ is as hereinbefore defined) or an acylating derivative thereof, it is possible, if desired, to demethylate the methoxy group in order to obtain a compound of general formula (I) wherein R₄ represents the hydroxy group.

If it is desired to prepare a compound of general formula (I) in the form of a single enantiomer, irrespective of the group —NR₂R₃, a step for the separation of the enantiomers of the primary amine of general formula (V) is introduced into the process [in this case, the final compounds of general formula (I) wherein —NR₂R₃ is a dialkylamino group will be prepared not by reaction of a dialkylamine of general formula (III) with the ketone of formula (II), but by direct alkylation of the separated enantiomer of the primary amine of formula (V)].

The resolution can be carried out by means of the formation of diastereoisomeric salts from chiral acids such as tartaric acid, mandelic acid, camphosulphonic acid and, preferably, dibenzoyltartaric acid.

The salification is carried out starting from a mixture of enantiomers of the primary amine of general formula (V), for example starting from the racemate obtained from the ketone of formula (II), in the form of the base, dissolved in a suitable solvent such as an alcohol, preferably ethanol. The two diastereoisomeric salts thus obtained are then separated by fractional crystallisation.

After the separation, they can be separated from the chiral acid, that is to say reconverted to the base, and then converted to an addition salt with another acid.

An enantiomer of general formula (V) can also be obtained from a base partially enriched in this enantiomer, originating, for example, from the mother liquors from the recrystallisation of a mixture of diastereoisomeric salts. The chiral acid used for the separation of such an enriched mixture is then the antipode of that which made it possible to obtain the enriched mixture.

Pharmacologically-acceptable acid addition salts of the tetrahydronaphthalene derivatives of general formula (I), e.g. methanesulphonates, mandelates, fumarates, maleates, malonates, citrates, hydrobromides and hydrochlorides, may be obtained by methods known per se, for example by treatment of the tetrahydronaphthalene base with the appropriate acid in a solvent medium, e.g. an alkanol or ether, or mixtures thereof.

By the term 'methods known per se' in this specification is meant methods heretofore used or described in the literature.

The following Examples illustrate the preparation of compounds of general formula (I) of the invention.

The analyses and the IR and NMR spectra confirm the structure of the compounds.

EXAMPLE 1

2-Dipropylamino-5-formylamino-6-hydroxy-1,2,3,4-tetrahydronaphthalene hydrobromide ($R_1$=CHO, $R_2$=$C_3H_7$, $R_3$=$C_3H_7$, $R_4$=OH)

(a) 2-Dipropylamino-6-methoxy-1,2,3,4-tetrahydronaphthalene 20 g of 6-methoxytetrahydronaphthalen-2-one, 20 ml of dipropylamine and 200 mg of para-toluenesulphonic acid are introduced into 300 ml of benzene under a nitrogen atmosphere. The mixture, which has become black, is then heated under reflux for 12 hours, the water of condensation being removed by azeotropic distillation. The solution, which contains the compound (IV), is then concentrated to a volume of about 100 ml. For the hydrogenation, 150 ml of ethanol and 300 mg of $PtO_2$ are added thereto and hydrogenation is carried out, under a pressure of about 0.3 MPa, until the absorption has stopped.

After removal of the catalyst, the solvents are driven off under reduced pressure and the residual black oil is taken up in toluene and extracted with N hydrochloric acid. The hydrochloric acid solution is then neutralised with an alkali and extracted with toluene, the organic phase is dried and filtered on 200 g of neutral alumina, and elution is completed by means of methylene chloride. Concentration gives a virtually colourless oil.

(b) 2-Dipropylamino-6-methoxy-5(and 7)-nitro-1,2,3,4-tetrahydronaphthalene 21 g of 2-dipropylamino-6-methoxy-1,2,3,4-tetrahydronaphthalene are added to 60 ml of trifluoroacetic acid, with simultaneous cooling of the mixture. 7 ml of nitric acid (d=2.42) are then added dropwise, the temperature being kept at about 0° C. The mixture is stirred for a further 10 minutes, the whole is poured into water and the insoluble material is extracted with methylene chloride; the organic phase is shaken with a solution of potassium carbonate and washed with water.

After drying and evaporation, the brown gum obtained is subjected to chromatography on a column of neutral alumina (800 g), elution being carried out with toluene. The less polar compound is the isomer nitrated in the 5-position. 9 g of each of the isomers are obtained. The compound nitrated in the 5-position melts at 198°-220° C. and the compound nitrated in the 7-position melts at 158°-160° C. (in the form of the hydrochlorides).

(c) 2-Dipropylamino-6-hydroxy-5-nitro-1,2,3,4-tetrahydronaphthalene hydrobromide 9 g of 2-dipropylamino-6-methoxy-5-nitro-1,2,3,4-tetrahydronaphthalene are introduced into 100 ml of 48% hydrobromic acid and the mixture is heated under reflux for 2 hours. The acid is then driven off under reduced pressure and the residue is taken up three times in water, the water being evaporated off each time in order to remove any trace of acid. When recrystallised from water, the solid obtained forms a monohydrate which melts at 236° C. (with decomposition).

(d) 2-Dipropylamino-5-amino-6-hydroxy-1,2,3,4-tetrahydronaphthalene hydrobromide 7 g of 2-dipropylamino-6-hydroxy-5-nitro-1,2,3,4-tetrahydronaphthalene hydrobromide are suspended in 250 ml of ethanol and hydrogenation is carried out at ambient temperature, in the presence of 1 g of 5% palladium-on-charcoal, under a pressure of about 0.3 MPa. The solvent is then evaporated off and the residue is triturated in diethyl ether. The product obtained melts at 215°-218° C. (with decomposition).

(e) 2-Dipropylamino-5-formylamino-6-hydroxy-1,2,3,4-tetrahydronaphthalene hydrobromide 0.42 ml of acetic anhydride is added all at once to 2 ml of 98% formic acid, kept at 0° C., and the mixture is left at 0° C. for 15 minutes. Then, still using an ice-bath, 1.34 g of 2-dipropylamino-5-amino-6-hydroxy-1,2,3,4-tetrahydronaphthalene hydrobromide are introduced therein with a spatula and the whole is stirred for one hour at 0° C.

After diethyl ether has been added and the solid filtered off, the latter is recrystallised from the minimum amount of ethanol. This gives the title compound melting at 199° C.

EXAMPLE 2

2-Dipropylamino-7-formylamino-6-hydroxy-1,2,3,4-tetrahydronaphthalene hydrobromide ($R_1$=CHO, $R_2$=$C_3H_7$, $R_3$=$C_3H_7$, $R_4$=OH)

(a) 2-Dipropylamino-7-amino-6-methoxy-1,2,3,4-tetrahydronaphthalene 9 g of the 2-dipropylamino-6-methoxy-7-nitro-1,2,3,4-tetrahydronaphthalene obtained in accordance with Example 1(b) are introduced into 200 ml of ethanol, together with 1 g of Raney nickel. At ambient temperature, hydrogenation is carried out under pressure until the absorption has stopped. After evaporation of the solvent, an oil remains which is shown to oxidise fairly readily in air.

(b) 2-Dipropylamino-7-amino-6-hydroxy-1,2,3,4-tetrahydronaphthalene dihydrobromide The product obtained above is introduced in 100 ml of 48% hydrobromic acid, the mixture is heated under reflux for 10 hours and the acid is then driven off under reduced pressure and subsequently removed completely by distillation with a toluene/ethanol mixture in a rotary evaporator. After recrystallisation from isopropyl alcohol, the dihydrobromide melts at 250° C. (with decomposition).

(c) 2-Dipropylamino-7-amino-6-hydroxy-1,2,3,4-tetrahydronaphthalene monohydrobromide A solution of 5 ml of Amberlite LA2 resin in 50 ml of petroleum ether is added to a solution of 3 g of the dihydrobromide obtained in (b) above in 50 ml of water. The mixture is shaken for 15 minutes at ambient temperature and the aqueous phase is separated off and evaporated to dryness in order to isolate the crude monohydrobromide, in an amorphous and coloured form, which is used as such for the formylation.

(d)
2-Dipropylamino-7-formylamino-6-hydroxy-1,2,3,4-tetrahydronaphthalene hydrobromide 0.7 ml of acetic anhydride is added to 3 ml of 98% formic acid, kept at 0° C., and the whole is left for 15 minutes at 0° C. 2.2 g of 2-dipropylamino-7-amino-6-hydroxy-1,2,3,4-tetrahydronaphthalene hydrobromide are then added thereto and the mixture is then stirred for one hour at 0° C. After 50 ml of diethyl ether have been added and the solid has been filtered off, the latter is recrystallised from a 50/50 methanol/ethyl acetate mixture. This gives 1 g of the final product melting at 213° C. (with decomposition).

EXAMPLE 3
2-Dipropylamino-5-acetylamino-6-hydroxy-1,2,3,4-tetrahydronaphthalene hydrobromide ($R_1$=COCH$_3$, $R_2$=C$_3$H$_7$, $R_3$=C$_3$H$_7$, $R_4$=OH)

10 ml of acetic acid and 0.46 ml of acetic anhydride are added to 1.5 g of 2-dipropylamino-5-amino-6-hydroxy-1,2,3,4-tetrahydronaphthalene hydrobromide (obtained in accordance with Example 1(d)) in 25 ml of methylene chloride at 0° C. The mixture is stirred for one hour, diethyl ether is added and the solid is recrystallised from ethanol. This gives 1.2 g of a product melting at 244.5° C.

EXAMPLE 4
2-Amino-6-hydroxy-7-formylamino-1,2,3,4-tetrahydronaphthalene hydrochloride ($R_1$=CHO, $R_2$=H, $R_3$=H, $R_4$=OH)

(a) 2-Amino-6-methoxy-1,2,3,4-tetrahydronaphthalene hydrochloride

A mixture of 10 g of 6-methoxytetrahydronaphthalen-2-one in 150 ml of benzene and of 5.9 ml of benzylamine is heated under reflux for two hours with 100 mg of para-toluenesulphonic acid under a nitrogen atmosphere. The water of condensation is removed by azeotropic distillation. The mixture is concentrated to a volume of 100 ml and subjected to catalytic hydrogenation, in the presence of 100 mg of PtO$_2$, under a pressure of 0.3 MPa and at ambient temperature. The catalyst is removed by filtration and 4.7 ml of 12 N hydrochloric acid are added to the filtrate.

A second hydrogenation is then carried out, in the presence of 1 g of palladium-on-charcoal, at about 60° C. and at a pressure of the order of 0.35 MPa.

The catalyst is removed, the solvents are driven off under reduced pressure and the product formed is recrystallised from isopropyl alcohol; it melts at 254° C.

(b)
2-Acetylamino-6-methoxy-1,2,3,4-tetrahydronaphthalene

2-Amino-6-methoxy-1,2,3,4-tetrahydronaphthalene hydrochloride is dissolved in a mixture of water and methylene chloride, and 10 N sodium hydroxide solution is added thereto until the pH is 12. 1.5 equivalents of acetic anhydride are then added, the pH being kept between 10 and 12 with 10 N sodium hydroxide solution, and the mixture being cooled to about 15° C. The pH is then brought to between 7 and 8 and the organic phase is separated off, dried and evaporated. When recrystallised from petroleum ether, the residue melts at 175° C.

(c)
2-Acetylamino-7-nitro-6-methoxy-1,2,3,4-tetrahydronaphthalene 30 g of 2-acetylamino-6-methoxy-1,2,3,4-tetrahydronaphthalene are introduced in small amounts into 600 ml of nitric acid (d=1.38), the temperature being kept between $-5°$ and $-10°$ C. The reaction has ended when total dissolution has taken place. The solution is then poured into 2 liters of water and ice and the solid is filtered off, washed and dried. This gives a mixture of the two mononitro isomers, the one being nitrated in the 5-position and the other in the 7-position, and of the dinitro compound. They are separated on a silica column with a 99/1 methyl ethyl ketone/methanol mixture. The compound nitrated in the 7-position melts at 175° C.

(d)
2-Acetylamino-7-amino-6-methoxy-1,2,3,4-tetrahydronaphthalene

Hydrogenation under the conditions described in Example 2(a) gives, with a quantitative yield, a product melting at 158° C.

(e)
2,7-Diamino-6-hydroxy-1,2,3,4-tetrahydronaphthalene dihydrochloride 2.7 ml of boron tribromide are added to a solution of 23 g of 2-acetamido-7-amino-6-methoxy-1,2,3,4-tetrahydronaphthalene in methylene chloride at $-60°$ C. The mixture is left to return to ambient temperature, cooled to $-60°$ C. and neutralised with methanol. After evaporation to dryness, 12 N hydrochloric acid is added and the mixture is heated under reflux for 48 hours. It is then left to cool and the crystals formed are filtered off, washed with acetone and then with diethyl ether and dried. The product collected melts above 300° C.

(f)
2-Amino-7-formylamino-6-hydroxy-1,2,3,4-tetrahydronaphthalene hydrochloride

A solution of 5 ml of Amberlite LA2 resin in 50 ml of petroleum ether is added to a solution of 2 g of 2,7-diamino-6-hydroxy-1,2,3,4-tetrahydronaphthalene dihydrochloride in 50 ml of water. The mixture is stirred for 15 minutes at ambient temperature and the aqueous phase is collected and evaporated to dryness. This gives the monohydrochloride in a quantitative yield. 0.83 ml of acetic anhydride is then added to 3 ml of formic acid in an ice-bath and the mixture is left for 15 minutes at 0° C. Still using the ice-bath, 1.69 g of the 2,7-diamino-6-hydroxy-1,2,3,4-tetrahydronaphthalene hydrochloride obtained as described above are then added thereto and the mixture is stirred for a further one hour. After diethyl ether has been added and the solid has been filtered off, the latter is recrystallised from the minimum amount of ethanol. It melts at 235° C. (with decomposition).

EXAMPLE 5

2-Dipropylamino-7-hydroxy-8-formylamino-1,2,3,4-tetrahydronaphthalene hydrobromide ($R_1$=CHO, $R_2$=$C_3H_7$, $R_3$=$C_3H_7$, $R_4$=OH)

(a)

2-Dipropylamino-7-methoxy-1,2,3,4-tetrahydronaphthalene

A mixture of 20 g of 7-methoxytetrahydronaphthalen-2-one and 20 ml of dipropylamine in 200 ml of benzene is heated under reflux for 15 hours with 500 mg of para-toluenesulphonic acid, the water of condensation being distilled off.

The benzene is then evaporated off and 100 ml of ethanol and 500 mg of $PtO_2$ are added. Hydrogenation is carried out at ambient temperature, under a pressure of the order of 0.35 MPa, until the absorption has ended, the catalyst is removed, the alcohol is evaporated off, the product is poured into 1 N hydrochloric acid, the solution is washed with toluene, neutralised with an alkali, extracted with toluene and dried. The organic phase thus obtained is filtered on neutral alumina, which is washed with toluene, and the filtrate is evaporated. 24 g of a colourless oil remain.

(b)

2-Dipropylamino-8-nitro-7-methoxy-1,2,3,4-tetrahydronaphthalene

The nitration of the product of (a) is carried out as in Example 1(b) and the two isomers are separated. The derivative nitrated in the 8-position is in the form of an oil.

(c)

2-Dipropylamino-8-amino-7-methoxy-1,2,3,4-tetrahydronaphthalene

The reduction is carried out as in Example 1(c).

(d)

2-Dipropylamino-8-amino-7-hydroxy-1,2,3,4-tetrahydronaphthalene dihydrobromide

The demethylation is carried out under the conditions of Example 2(b). The product obtained melts at 270° C. (with decomposition).

(e)

2-Dipropylamino-8-amino-7-hydroxy-1,2,3,4-tetrahydronaphthalene hydrobromide

The dihydrobromide of the product of (d) is treated with an Amberlite LA2 resin, as described above, to give the amorphous crude monohydrobromide, which is used as such.

(f)

2-Dipropylamino-8-formylamino-7-hydroxy-1,2,3,4-tetrahydronaphthalene hydrobromide The formylation of the product of (c) is carried out under the same conditions as those described in Example 2(d). The title compound melts at 232.5° C.

EXAMPLE 6

2-Propylamino-6-hydroxy-5-formylamino-1,2,3,4-tetrahydronaphthalene hydrobromide ($R_1$=CHO, $R_2$=H, $R_3$=$C_3H_7$, $R_4$=OH)

(a)

2-Propanoylamino-6-methoxy-1,2,3,4-tetrahydronaphthalene 46 g of 2-amino-6-methoxy-1,2,3,4-tetrahydronaphthalene hydrochloride (prepared in accordance with Example 4(a)) are introduced into 200 ml of water and 300 ml of methylene chloride. The pH is adjusted to 12 with 10 N sodium hydroxide solution. Then, with the mixture in an ice-bath, 40 ml of propionic anhydride are added thereto, the pH being simultaneously kept at 12. The two phases which have formed are separated, the organic phase is dried and concentrated to dryness, the residue is taken up in diethyl ether, the mixture is filtered and the material on the filter is dried. This gives 45 g of the acylated derivative, which melts at 125° C.

(b)

2-Propanoylamino-5-nitro-6-methoxy-1,2,3,4-tetrahydronaphthalene 12.2 g of 2-propanoylamino-6-methoxy-1,2,3,4-tetrahydronaphthalene are introduced into 100 ml of trifluoroacetic acid, and 3 ml of nitric acid (d=1.49) are added dropwise thereto. Stirring is continued for 8 hours and the mixture is then taken up in water and diethyl ether. To separate the nitro isomers, the mixture is subjected to chromatography under pressure, on a silica column, elution being carried out with an 8/2 methylene chloride/ethyl acetate mixture. 5 g of the isomer nitrated in the 7-position and 3.8 g of the isomer nitrated in the 5-position are finally collected.

(c)

2-Propanoylamino-5-amino-6-methoxy-1,2,3,4-tetrahydronaphthalene 1.8 g of the isomer nitrated in the 5-position, prepared as described in (b) above, in suspension in 50 ml of methanol, are hydrogenated under the conditions of Example 1(d). After the catalyst has been filtered off and the solvent has been evaporated off, 1.4 g of a product, melting at 141° C., are collected.

(d)

2-Propylamino-5-amino-6-methoxy-1,2,3,4-tetrahydronaphthalene 0.46 g of lithium aluminium hydride is introduced into 30 ml of tetrahydrofuran, a solution of 2.56 g of 2-propanoylamino-5-amino-6-methoxy-1,2,3,4-tetrahydronaphthalene in 50 ml of tetrahydrofuran is then added and the mixture is heated under reflux for 24 hours. It is then cooled and hydrolysed with a 2 N solution of sodium hydroxide, in an ice-bath. The organic phase is separated off, dried and concentrated to dryness. After chromatography on silica with a 1/1 diethyl ether/methanol mixture, 1.8 g of a yellowish oil are collected.

(e)

2-Propylamino-5-amino-6-hydroxy-1,2,3,4-tetrahydronaphthalene hydrobromide 50 ml of 48% hydrobromic acid containing 1.5 g of 2-propylamino-5-amino-6-methoxy-1,2,3,4-tetrahydronaphthalene are heated under reflux for 10 hours. 1.8 g of the dihydrobromide are then collected by concentrating the reaction medium. By following the procedure of Example 2(c), 1.19 g of the monohydrobromide are collected, melting at 280° C.

(f)
2-Propylamino-5-formylamino-6-hydroxy-1,2,3,4-tetrahydronaphthalene hydrobromide 1.9 g of 2-propylamino-5-amino-6-hydroxy-1,2,3,4-tetrahydronaphthalene hydrobromide are introduced into a mixture of 6 ml of formic acid and 0.67 ml of acetic anhydride, kept in an ice-bath for ½ hour. The mixture is stirred for 3 hours at ambient temperature and then poured into diethyl ether. The precipitate which has formed is filtered off and washed with hot isopropyl alcohol. After drying, 1.7 g of the final compound are obtained, which melts at 210° C.

EXAMPLES 7 to 23

Other compounds, prepared by analogous methods, are illustrated in Table I below by indicating their structure and their physical properties.

Table II illustrates the structures and physical properties of a few intermediates of formulae VI and VII.

TABLE II

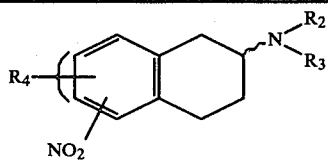

| Position of $NO_2$ | $R_2$ | $R_3$ | $R_4$ | Melting point (°C.) | Salt |
|---|---|---|---|---|---|
| 5 | $C_3H_7$ | $C_3H_7$ | (6)-$OCH_3$ | 198–200 | HCl |
| 7 | $C_3H_7$ | $C_3H_7$ | (6)-$OCH_3$ | 158–160 | HCl |
| 5 | $C_3H_7$ | $C_3H_7$ | (6)-OH | 236 | HBr |
| 5 | $CH_3$ | $CH_3$ | (6)-$OCH_3$ | 243–244 | HCl |
| 7 | $CH_3$ | $CH_3$ | (6)-$OCH_3$ | 240–241 | HCl |
| 5 | $C_3H_7$ | $C_3H_7$ | (6)-$OCH_3$ | $[\alpha]_D^{25} = -140°$ | HCl |
| 7 | $C_3H_7$ | $C_3H_7$ | (6)-$OCH_3$ | $[\alpha]_D^{25} = -76°$ | HCl |

EXAMPLE 24

Enantiomers of 2-dipropylamino-5-formylamino-6-hydroxy-1,2,3,4-tetrahydronaphthalene hydrobromide (a) 2-Amino-6-methoxy-1,2,3,4-tetrahydronaphthalene The procedure of Example 4(a) is followed and the hydrochloride is converted to the base in a known manner, for example by evaporating the organic phase of a mixture of methylene chloride, water and sodium hy-

TABLE I

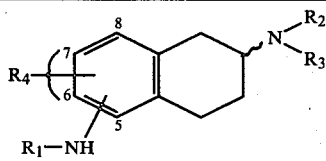

| Example | —NH—$R_1$ | $R_2$ | $R_3$ | $R_4$ | Melting point (°C.) | Salt* |
|---|---|---|---|---|---|---|
| 1 (d) | (5)-$NH_2$ | $C_3H_7$ | $C_3H_7$ | (6)-OH | 215–218 | HBr |
| 1 (e) | (5)-NH—CHO | $C_3H_7$ | $C_3H_7$ | (6)-OH | 199 | HBr |
| 2 (d) | (7)-NH—CHO | $C_3H_7$ | $C_3H_7$ | (6)-OH | 213 | HBr |
| 3 | (5)-NH—$COCH_3$ | $C_3H_7$ | $C_3H_7$ | (6)-OH | 244–245 | HBr |
| 4 (e) | (7)-$NH_2$ | H | H | (6)-OH | 300 | di-HCl |
| 4 (f) | (7)-NH—CHO | H | H | (6)-OH | 235 | HCl |
| 5 (f) | (8)-NH—CHO | $C_3H_7$ | $C_3H_7$ | (7)-OH | 232.5 | HBr |
| 6 (e) | (5)-$NH_2$ | H | $C_3H_7$ | (6)-OH | 280 | HBr |
| 6 (f) | (5)-NH—CHO | H | $C_3H_7$ | (6)-OH | 210 | HBr |
| 7 | (7)-NH—$COCH_3$ | $C_3H_7$ | $C_3H_7$ | (6)-$OCH_3$ | 168–169 | Mal |
| 8 | (7)-NH—$COCH_3$ | $C_3H_7$ | $C_3H_7$ | (6)-OH | 228–229 | HBr |
| 9 | (7)-NH—CHO | H | $C_3H_7$ | (6)-OH | 226 | HBr |
| 10 | (7)-$NH_2$ | $C_2H_5$ | $C_2H_5$ | (6)-$OCH_3$ | 208–209 | HCl |
| 11 | (5)-$NH_2$ | $C_2H_5$ | $C_2H_5$ | (6)-$OCH_3$ | 197–198 | HCl |
| 12 | (5)-NH—CHO | $C_2H_5$ | $C_2H_5$ | (6)-$OCH_3$ | 196–197 | HCl |
| 13 | (7)-NH—CHO | $C_2H_5$ | $C_2H_5$ | (6)-$OCH_3$ | 236–237 | HCl |
| 14 | (7)-NH—CHO | $C_2H_5$ | $C_2H_5$ | (6)-OH | 199–200 | HBr |
| 15 | (7)-$NH_2$ | $CH_3$ | $CH_3$ | (6)-$OCH_3$ | 134–135 | Mal |
| 16 | (5)-$NH_2$ | $CH_3$ | $CH_3$ | (6)-$OCH_3$ | 167–168 | Mal |
| 17 | (7)-NH—CHO | $CH_3$ | $CH_3$ | (6)-$OCH_3$ | 149–150 | Mal |
| 18 | (5)-NH—CHO | $CH_3$ | $CH_3$ | (6)-$OCH_3$ | 181–182 | Mal |
| 19 | (7)-$NH_2$ | $CH_3$ | $CH_3$ | (6)-OH | 227–228 | HBr |
| 20 | (7)-NH—CHO | $CH_3$ | $CH_3$ | (6)-OH | 217–218 | HBr |
| 21 | (5)-NH—CHO | $CH_3$ | $CH_3$ | (6)-OH | 264–265 | HBr |
| 22 | (7)-NH—$COCH_3$ | H | H | (6)-OH | 228 | HBr |
| 23 | (5)-NH—CHO | H | H | (6)-OH | >300 | HBr |
| 24 | (5)-$NH_2$ | $C_3H_7$ | $C_3H_7$ | (6)-OH | $[\alpha]_D^{25} = -32°$ | HBr |
|  | (5)-NH—CHO | $C_3H_7$ | $C_3H_7$ | (6)-OH | $[\alpha]_D^{25} = -48°$ | HBr |
| 25 | (7)-$NH_2$ | $C_3H_7$ | $C_3H_7$ | (6)-OH | $[\alpha]_D^{25} = -70°$ | HBr |
|  | (7)-NH—CHO | $C_3H_7$ | $C_3H_7$ | (6)-OH | $[\alpha]_D^{25} = -68°$ | HBr |

*HBr: hydrobromide
HCl: hydrochloride
Mal: maleate droxide, into which the hydrochloride has been introduced.

(b) Separation of the enantiomers of 2-amino-6-methoxy-1,2,3,4-tetrahydronaphthalene A solution of 6 g of L(−)-dibenzoyltartaric acid in 100 ml of ethanol is added rapidly to 5.5 g of the racemic amine (base), obtained as indicated above, in solution in 100 ml of ethanol. The heterogeneous medium thus obtained is concentrated under reduced pressure, the concentrate is taken up in diethyl ether and, after filtration and drying, 11 g of a salt which contains ½ mol of L(−)-dibenzoyltartaric acid are collected. This salt is recrystallised twice from ethanol containing 30% of water. The product obtained melts at 220°–221° C. By converting it to the hydrochloride, an optically active salt is obtained which melts at 254° C. (with decomposition) and has an optical rotation of $[\alpha]_D^{25} = -73°(c=1, \text{MeOH})$.

To isolate the other enantiomer, the ethanolic mother liquors from recrystallisation of the L(−)-dibenzoyltartrate are concentrated, the base form of the amine is re-formed and, after it has been extracted, the D(+)-dibenzoyltartrate thereof is precipitated by adding the corresponding acid. After recrystallisation, the D(+)-benzoyltartrate melts at 220°–221° C. By formation of the hydrochloride, an optically active salt is obtained which has an optical rotation of $[\alpha]_D^{25} = +73°(c=1, \text{MeOH})$.

(c) (−)-2-Dipropylamino-6-methoxy-1,2,3,4-tetrahydronaphthalene hydrochloride 15 ml of a saturated solution of potassium carbonate and then 9 ml of iodopropane are added to 1.9 g of the laevorotatory hydrochloride obtained as indicated above, in suspension in 20 ml of benzene. The mixture is stirred at the reflux temperature for 72 hours. The organic phase is then diluted with diethyl ether, and the hydrochloride is formed by adding a solution of hydrogen chloride in diethyl ether and isolated in the usual manner. It melts at 154° C. and has an optical rotation of $[\alpha]_D^{25} = -2.2°(c=1, \text{MeOH})$.

(d) (−)-2-Dipropylamino-5-formylamino-6-hydroxytetrahydronaphthalene hydrobromide The procedure of Example 1(b), (c), (d) and (e) is followed, using the enantiomer prepared as indicated above instead of the racemic mixture.

The hydrochlorides of the intermediates nitrated in the 5-position and 7-position have respective optical rotations of $[\alpha]_D^{25} = -140°$ and $D^{25} = -76°(c=1, \text{MeOH})$.

The reduced intermediate hydrobromide (NH$_2$ in the 5-position) has an optical rotation of −32° (c=1, MeOH).

The hydrobromide of the final compound, which is the laevorotatory enantiomer of the compound prepared in accordance with Example 1, has an optical rotation of $[\alpha]_D^{25} = -48°(c=1, \text{MeOH})$.

The compounds of the invention were subjected to pharmacological tests which demonstrated their antihypertensive and antiparkinson activity.

Thus, it was found that in rats or dogs anaesthaetised with sodium pentobarbital, the blood pressure dropped markedly after intravenous injections of 10 to 100 µg/kg animal body weight.

Furthermore, when administered intravenously or intraduodenally to dogs, the compounds of the invention inhibit the responses to electric stimulations of the nictitating membrane and of the heart, their activity in this case being about 20 times greater than that of the known dopaminergic N,N-dipropyldopamine.

The effects of the compounds of the invention are blocked by the action of sulpiride, a known antagonist of dopamine.

The antiparkinson activity of the compounds of the invention was demonstrated by the test for the antagonism towards the catalepsy induced by haloperidol.

It is known that, in rats, a certain number of neuroleptics induce a cataleptic state considered to be the reflection of a blocking of the dopaminergic receptors in the extrapyramidal system: this is the case of haloperidol, the cataleptigenic effect of which is antagonised by the dopaminergic agonists such as apomorphine or amphetamine, by the tricyclic antidepressants and by the anticholinergics.

The method used in this case is a modification of that described by Tedeschi et al., Arch. Int. Pharmacodyn. (1959) 122, 129.

The haloperidol is administered intraperitoneally to the rats at a dose of 1 mg/kg animal body weight in a volume of 1 ml/100 g of body weight.

Thirty minutes after this injection, the products to be studied are administered to 6 rats per dose and at a rate of 3 doses per product studied.

The catalepsy of the animals is evaluated 30 minutes (intraperitoneal administration) or 60 minutes (oral administration) after the administration of the product to be studied, and then every 30 minutes for 3 hours (intraperitoneal administration) or 4 hours (oral administration). To do this, each animal is placed in a position such that each paw is resting on a "stopper" of 25 mm in height and 12 mm in diameter.

The animal is considered to be cataleptic if it remains in this position for at least 10 seconds.

The average percentage of cataleptic animals, and then the percentage decrease relative to the control animals, are calculated for each dose and each product.

The AD50, namely the dose which antagonises the cataleptic effect of the haloperidol by 50%, is determined graphically.

It was thus found that the AD50 of the compounds of the invention was of the order of 7 mg/kg animal body weight, both by intraperitoneal administration and by oral administration.

Finally, their acute toxicity in mice is of the order of 90 mg/kg animal body weight, administered intravenously, and of the order of 150 mg/kg animal body weight, administered orally.

Taking account of their properties, the compounds of the invention can be used for the treatment of cardiovascular diseases, in particular for the treatment of hypertension, and also for the treatment of Parkinson's disease. They can be administered orally, rectally or parenterally in daily doses of 1 to 500 mg per unit doses containing, for example, 1 to 100 mg of active substance.

The invention includes pharmaceutical compositions containing, as active principle, the compounds of general formula (I), and their pharmaceutically-acceptable acid addition salts, in association with any excipients suitable for their oral, rectal or parenteral administration. These pharmaceutical compositions can also contain other medicinal substances with which these compounds and their salts are pharmaceutically and therapeutically compatible.

For oral administration, all the pharmaceutical forms suitable for this method of administration are used, that is to say tablets, coated tablets, gelatin capsules, capsules, cachets, and solutions and suspensions to be taken orally.

For endorectal administration, suppositories are used.

For parenteral administration, stabilised and buffered, injectable solutions are used which are prepared in advance or for immediate use.

We claim:

1. A 1,2,3,4-tetrahydronaphthalene derivative of the formula:

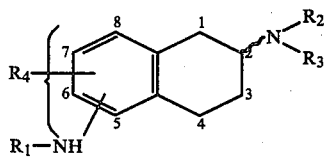

wherein $R_1$ represents an alkanoyl group containing from 1 to 4 carbon atoms, $R_2$ and $R_3$ each represent, independently of one another, a hydrogen atom or an alkyl group containing from 1 to 4 carbon atoms, and $R_4$ represents a hydroxy or methoxy group located in the 6-position or 7-position, and its pharmacologically-acceptable acid addition salts.

2. A tetrahydronaphthalene derivatives according to claim 1 wherein $R_1$ represents a formyl or acetyl group and $R_2$ and $R_3$ each represent a propyl group.

3. A tetrahydronaphthalene derivative according to claim 1 wherein the group —NH—$R_1$ is in the 5-position and $R_1$ represents a formyl or acetyl group, $R_2$ and $R_3$ each represent a propyl group, and $R_4$ represents a hydroxy or methoxy group located in the 6-position.

4. A tetrahydronaphthalene derivative according to claim 1 wherein the group —NH—$R_1$ is in the 5-position and $R_1$ represents a formyl or acetyl group, $R_2$ and $R_3$ each represent a propyl group, and $R_4$ represents a hydroxy group located in the 6-position.

5. A tetrahydronaphthalene derivative according to claim 1 which is 2-dipropylamino-5-formylamino-6-hydroxy-1,2,3,4-tetrahydronaphthalene and its pharmacologically-acceptable acid addition salts.

6. A pharmaceutical composition for the treatment of a patient with Parkinson's disease which comprises, as active ingredient, an effective amount of a tetrahydronaphthalene derivative of the formula depicted in claim 1 wherein $R_1$, $R_2$, $R_3$ and $R_4$ are as defined in claim 1, or a pharmaceutically-acceptable acid addition salt thereof, in association with any suitable pharmaceutically-acceptable vehicle.

7. A method for the treatment of a patient with Parkinson's disease which comprises administering to such patient a tetrahydronaphthalene derivative as claimed in any one of claims 1, 2, 3, 4 or 5, or a pharmacologically-acceptable acid addition salt thereof, in an amount effective to ameliorate the condition of the patient.

8. A method for the treatment of a patient with a cardiovascular disease which comprises administering to such patient a tetrahydronaphthalene derivative as claimed in any one of claims 1, 2, 3, 4 or 6, or a pharmacologically-acceptable acid addition salt thereof, in an amount effective to ameliorate the condition of the patient.

* * * * *